United States Patent
Stanley et al.

(10) Patent No.: US 7,527,373 B2
(45) Date of Patent: May 5, 2009

(54) SAFETY EYEWEAR

(75) Inventors: Glen Stanley, Woodstock, CT (US); Richard W. Canavan, Woodstock, CT (US); Solomon Marini, Littleton, MA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/758,868

(22) Filed: Jun. 6, 2007

(65) Prior Publication Data

US 2007/0279578 A1 Dec. 6, 2007

Related U.S. Application Data

(60) Provisional application No. 60/811,325, filed on Jun. 6, 2006.

(51) Int. Cl.
*G02C 9/00* (2006.01)
(52) U.S. Cl. .......................... 351/47; 351/57
(58) Field of Classification Search ................. 351/103, 351/106, 43, 83, 86, 41, 47, 48, 57, 58; 2/428, 2/426, 438, 434, 436
See application file for complete search history.

(56) References Cited

U.S. PATENT DOCUMENTS

| 5,410,763 | A | 5/1995 | Bolle |
| 5,457,503 | A | 10/1995 | Chen |
| 5,682,621 | A | 11/1997 | Park |
| 6,959,988 | B1 * | 11/2005 | Sheldon ........................ 351/106 |
| 7,058,990 | B1 * | 6/2006 | Lan ................. 2/428 |
| 7,200,875 | B2 * | 4/2007 | Dondero ......................... 2/436 |
| 2003/0221246 | A1 | 12/2003 | Schary et al. |
| 2004/0025232 | A1 | 2/2004 | Hartley et al. |
| 2004/0117898 | A1 | 6/2004 | Penque, Jr. et al. |
| 2005/0036104 | A1 | 2/2005 | Howard et al. |

FOREIGN PATENT DOCUMENTS

| EP | 1008369 A1 | 6/2000 |
| EP | 1262211 A1 | 12/2002 |
| EP | 1550898 A1 | 7/2005 |
| WO | WO9741815 | 11/1997 |
| WO | WO2005043220 | 5/2005 |

OTHER PUBLICATIONS

International Search Report and Written Opinion; PCT/US2007/013370; Jan. 23, 2008.
International Search Report and Written Opinion; PCT/US2007/013345; Jul. 11, 2007.
International Search Report and Written Opinion; PCT/US2007/013344; Oct. 30, 2007.

* cited by examiner

*Primary Examiner*—Hung X Dang
(74) *Attorney, Agent, or Firm*—Cantor Colburn LLP

(57) ABSTRACT

Exemplary embodiments include a safety eyewear including: a lens permanently attached to a removable lens carrier; and a frame removably attached to the removable lens carrier, the removable lens carrier and the frame extend from a bottom of a side portion of the lens across an upper portion of the lens to a bottom of an opposite side portion of the lens wherein the safety eyewear provides a user with an unobstructed field of vision during use.

6 Claims, 5 Drawing Sheets

SAFETY EYEWEAR

CROSS REFERENCE TO RELATED APPLICATIONS

The present application claims priority to U.S. Provisional Patent Application Ser. No. 60/811,181, filed Jun. 6, 2006, the entire contents of which are specifically incorporated herein by reference.

BACKGROUND

1. Field

The present disclosure generally relates to safety eyewear frames and lenses. More particularly, the present disclosure relates to a safety eyewear assembly that provides a user with an unobstructed field of vision in the vertical direction.

2. Description of the Related Art

Safety eyewear is worn for a variety of safety reasons. As a result, a variety of safety eyewear types, each specifically designed and intended for a particular use or a particular environment, has been developed. For example, safety eyewear is often worn to protect a wearer's eyes from debris during metal machining operations, military operations, and the like. In such an environment, metal shards, sand or other debris may be propelled towards an operator's eyes. Safety eyewear is also worn in the chemical industries to protect employees from airborne chemicals resulting from splashes or spills. Still further safety eyewear is worn in industries utilizing lasers. Lasers can be damaging to the eye if exposed. Lasers are particularly dangerous because different wavelengths of laser light may require different lenses for filtering the damaging light.

Because of the proliferation of safety requirements now requiring greater numbers of employees to wear safety eyewear, cost, ease of replacement of the lenses, the ability to accommodate prescription lenses, and fashion have now become prime concerns for customers of these safety products.

SUMMARY

Exemplary embodiments include a safety eyewear including: a lens permanently attached to a removable lens carrier; and a frame removably attached to the removable lens carrier, the removable lens carrier and the frame extend from a bottom of a side portion of the lens across an upper portion of the lens to a bottom of an opposite side portion of the lens wherein the safety eyewear provides a user with an unobstructed field of vision in the vertical direction during use.

Additional features and advantages are realized through the techniques of the present invention. Other embodiments and aspects of the invention are described in detail herein and are considered a part of the claimed invention. For a better understanding of the invention with advantages and features, refer to the description and to the drawings.

The detailed description explains exemplary embodiments of the invention, together with advantages and features, by way of example with reference to the drawings.

DETAILED DESCRIPTION

Referring now to the Figures for the purpose of illustration, it is to be understood that standard components or features that are within the purview of an artisan of ordinary skill and do not contribute to the understanding of the various exemplary embodiments are omitted from the Figures to enhance clarity.

Figure 1:
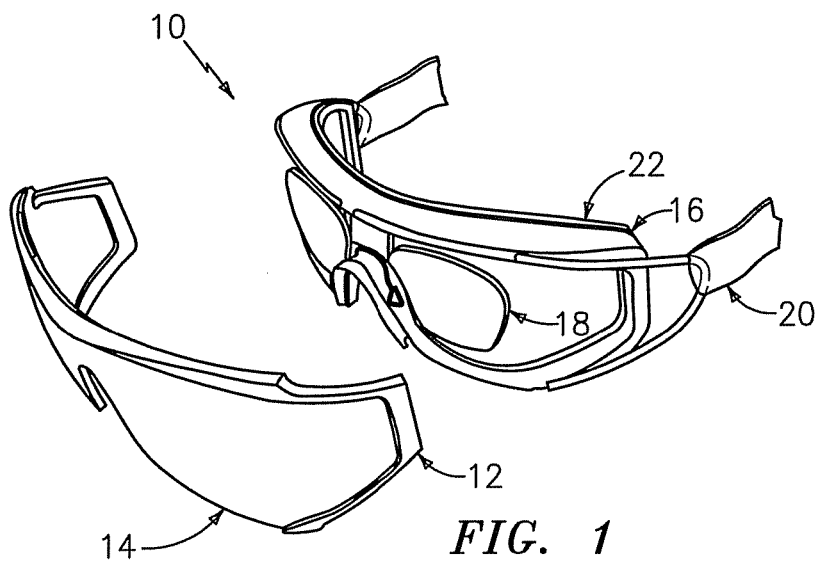
FIG. 1 illustrates exemplary safety eyewear including removable lens carrier with a prescription insert in accordance with exemplary embodiments.

FIG. 1 illustrates an exemplary safety eyewear 10 that includes a removable lens carrier 12, a lens 14, a frame 16, and a removable prescription insert 18. The removable lens carrier 12 is removably attached to the frame 16 and the removable prescription insert 18 is also removably attached to the frame 16. The safety eyewear 10 can also include a strap 20 is used to secure the safety eyewear 10 to the user.

In one embodiment, the frame 16 is made of a semi-flexible material, which provides a connection point for removable lens carrier 12. The frame 16 and the removable lens carrier 12 may connect to one another using a variety of attachment mechanisms including, but not limited to, a tongue and groove junction, a male and female flange connection, a latch, or the like. In one embodiment, the frame 16 and the removable lens carrier 12 may form an airtight seal. The frame 16 may also include a face seal gasket 22 that provides a seal between the frame 16 and the users face. The removable prescription inset 18 may be attached to or detached from the frame 16 when the removable lens carrier 12 is not attached to the frame 16.

The removable lens carrier 12 is removably attached to the frame 16 and permanently attached to the lens 14. The lens 14 may be provided with a variety of tints and coatings. The removable lens carrier 12 and the lens 14 may have a variety of shapes and sizes that are each specifically designed and intended for a particular use or a particular environment. The removable lens carrier 12 is designed such that a user may detach it from the frame 16 while the user is wearing the frame 16. For example, a user may be able to change the type of lens used without having to completely remove the safety eyewear 10. The removable lens carrier 12 allows the user to use a single safety eyewear in a variety of different environments and for a variety of different uses.

In exemplary embodiments, the removable lens carrier 12 may completely encase the lens 14 or may only partially encase the lens 14. In one embodiment, the removable lens carrier 12 may not cover, or attach to, a bottom portion of the lens 14, which may increases the available viewing angle to the user. For example, traditional safety goggles include a thick frame on the bottom portion of the safety goggles that may obstruct the user's field of vision in the vertical direction. The use of a removable lens carrier 12 that does not cover, or is attached to, the bottom portion of the lens 14 provides the user with an unobstructed field of vision in the vertical direction. Additionally, the frame 16 may also have a reduced thickness on the bottom portion of the safety eyewear 10 to provide an increased field of vision to the user. In an exemplary embodiment, the unobstructed portion comprises at least an two centimeters of lens bottom on each orbital wherein the frame is not overlying the viewable lens portion. In another exemplary embodiment, the unobstructed portion comprises at least an three centimeters of lens bottom on each orbital wherein the frame is not overlying the viewable lens portion.

Figure 2:
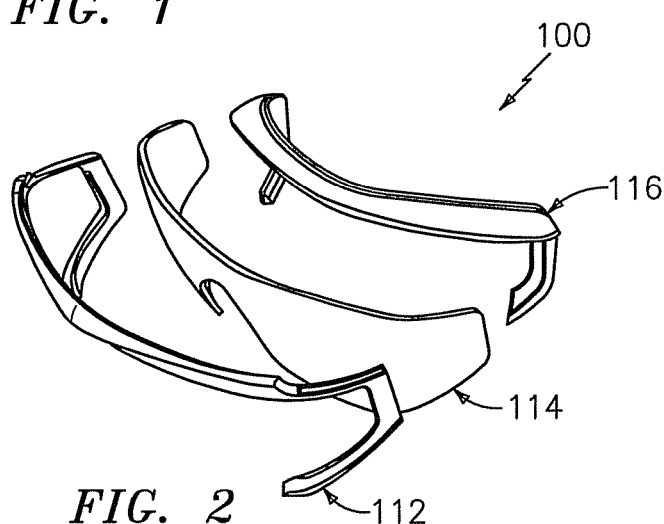
FIG. 2 illustrates another exemplary safety eyewear including a removable lens carrier in accordance with exemplary embodiments.

Referring now to FIG. 2, another exemplary safety eyewear 100 that includes a removable lens carrier 112, a lens 114, and a frame 116 is illustrated. The safety eyewear 100 is designed to provide an unobstructed field of vision to its user. Accordingly, the frame 116 extends from a lower portion of one side of the safety eyewear 100 across the top of the safety eyewear 100 to the lower portion of the opposite side of the safety eyewear 100. In addition the removable lens carrier 112 only covers the sides and upper portion of the lens 114 thereby providing the user with an unobstructed filed of vision.

Figure 3:
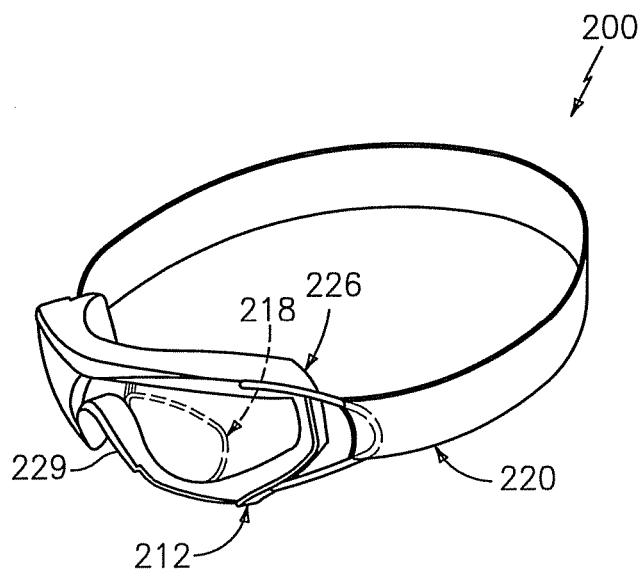
FIG. 3 illustrates exemplary safety eyewear including a removable lens carrier with a prescription insert in accordance with other exemplary embodiments.

Referring now to FIG. 3, another exemplary safety eyewear 200 includes a removable lens carrier 212, a frame 216, and a removable prescription insert 218 is illustrated. In one embodiment, the removable prescription insert 218 and a frame 216 are designed to securely connect to each other such that the removable prescription insert 218 remain properly positioned and connected to the frame 216 during the use of the safety eyewear 210. In one embodiment, the removable prescription insert 218 is attached to the frame 218 by pinching a nose portion of the frame 216. The removable prescription insert 218 may include a single lens or two lenses connected by a wire 224. The wire 224 may be used to attach the removable prescription 218 to the frame. For example, the wire 224 may pinch the nose portion of the frame 218 and/or may include an attachment portion, which may be inserted into a receptacle on the frame 218. The frame 216 may be designed to accommodate a variety of different shaped removable prescription inserts 218.

In one embodiment, the safety eyewear 200 may also include a strap 220 and a strap attachment device 226. The strap 220 may be adjustable in length and may be made of an elastic material. The strap 220 may be permanently or removably attached to the frame 216 by the attachment device 226. The attachment device 226 may include a variety of different devices. For example the attachment device 226 may be a loop extending from either side of the frame 216 and the strap may include a hook, Velcro, a buckle, or any other means for securing the strap 220 to the attachment device 226. In another example, the attachment device 226 may be a button that attaches the strap 220 to the frame 216.

In one embodiment, the attachment device 226 may be a flexible cable that is anchored in the frame 216. In one embodiment, the flexible cable may extend the entire length of the frame 216 and may provide structural support to the frame 216. The flexible cable provides a flexible attachment device 226 that allows the point of attachment between the frame 216 and the strap 220 to be adjusted to accommodate varying uses of the safety wear 210. The flexible cable may be in the shape of loop and permit a wide range of attachment angles for the strap 220. In one example, the safety eyewear 200 may be worn with a helmet and the flexible cable allows the user to selectively wear the strap 220 either above or below the surface of the helmet. In an alternative embodiment, the strap 220 may connect the frame 216 to a helmet worn by a user rather than connecting the two ends of the frame 216.

Figure 4A:
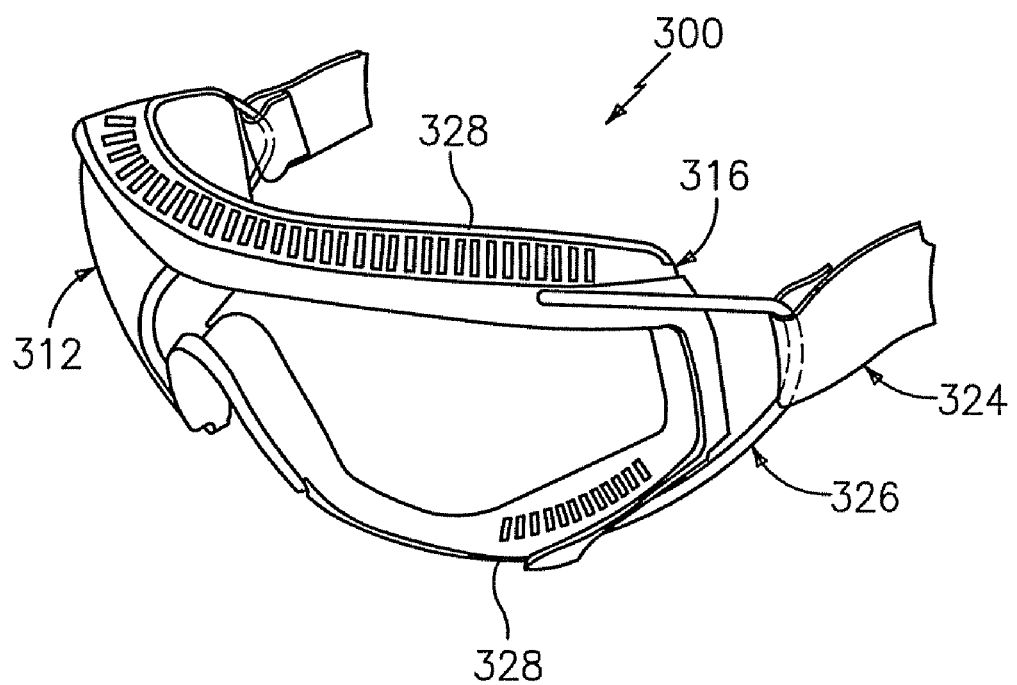
FIGS. 4(a)-(b) illustrates exemplary safety eyewear including an actuating vent in accordance with exemplary embodiment.
Figure 4B:
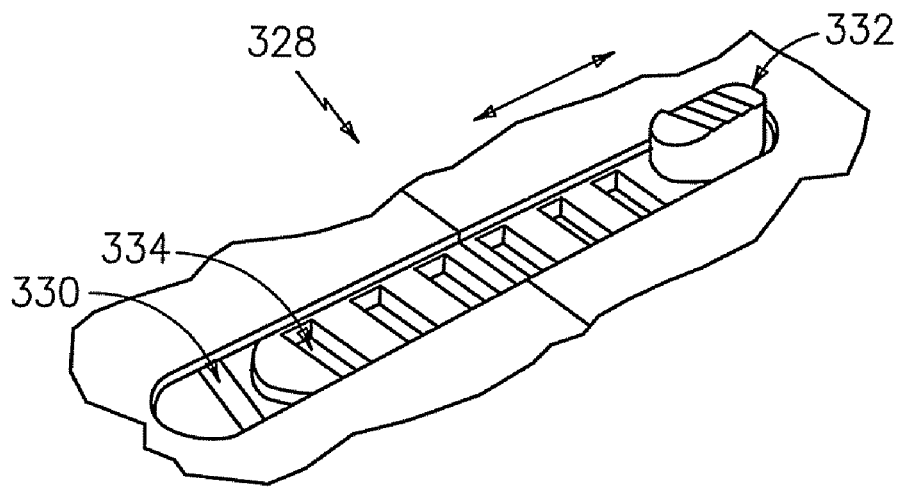

Referring now to FIGS. 4*a*-*b*, an exemplary safety eyewear 300 including an actuating vent 328 is illustrated. The safety eyewear also includes a removable lens carrier 312, a frame 316, a strap 324, and an attachment device 326. The actuating vent 328 may be disposed on a top and/or bottom portion of the frame 316. The actuating vent 328 includes a slide cover 332 that has a plurality of opening 334. The plurality of openings 334 are disposed on the slide cover 332 such that they selectively line up with a plurality of openings 330 in the frame 316. The slide cover 332 allows the user to open and close the actuating vent 328 to allow air to circulate inside of the safety eyewear 300.

Figure 5:
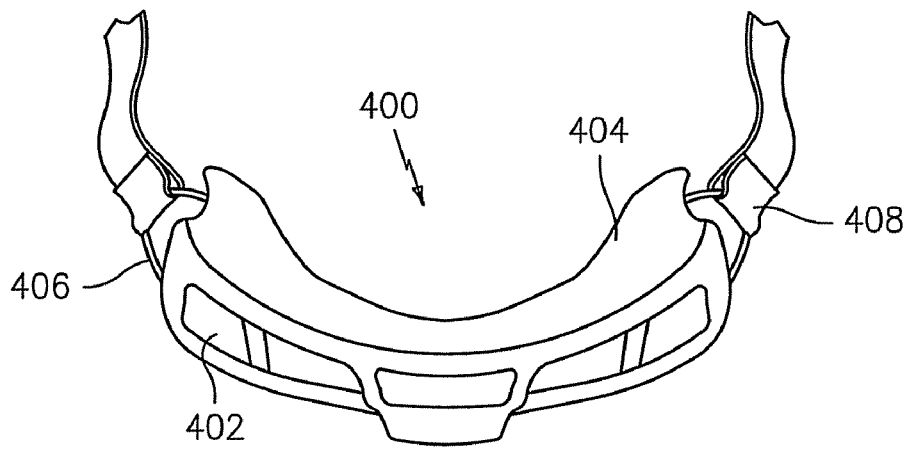
FIG. 5 is a top elevation view of an exemplary safety eyewear.

Referring now to FIG. 5, an exemplary safety eyewear 400 may also include mesh or similar venting 402 at least partially around the periphery of the eyewear frame 404. This embodiment also has a flexible cable 406 that is slidably attached to removable strap clip 408. This slidable connection, as well as the fact that the cable runs between both sides of the eyewear ensures that the eyewear will self compensate for position adjustments.

Figure 6:
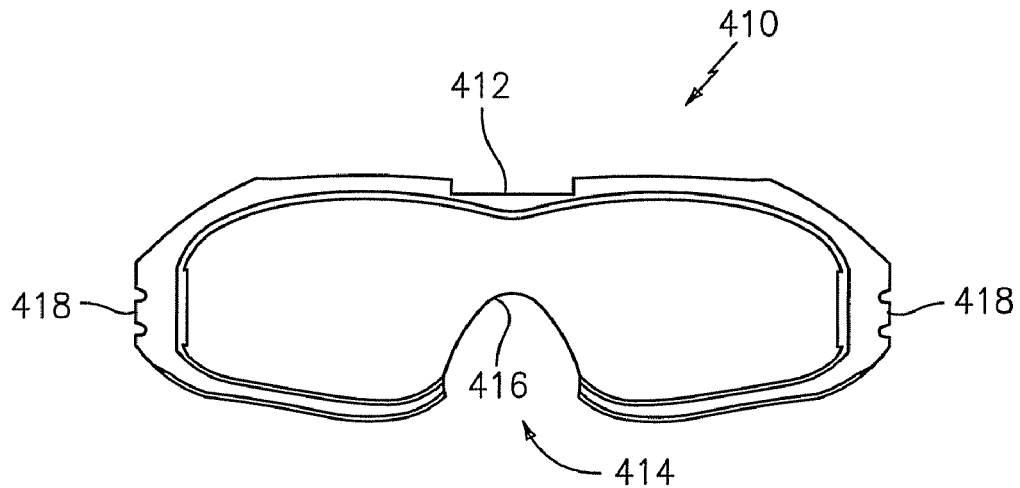
FIG. 6 is a a rear elevation view of an exemplary removable lens carrier.
Figure 7:
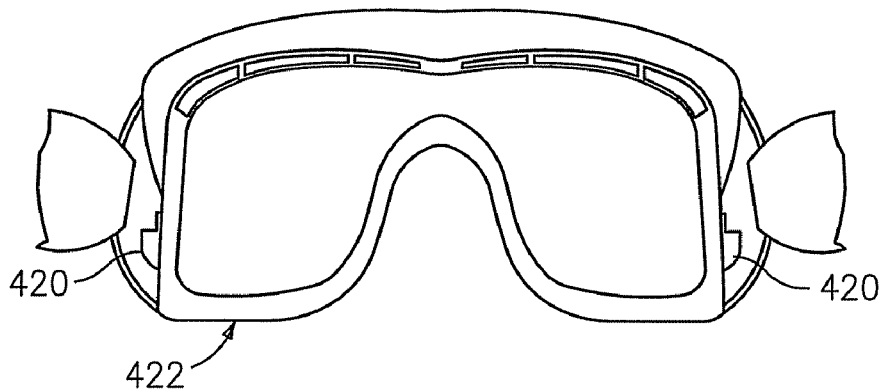
FIG. 7 is a front elevation view of an exemplary safety eyewear.

With reference to FIG. 6, an exemplary removable lens carrier 410 includes a top frame attachment point 412 (the top frame of the eyewear will overlie this point) and a bottom frame attachment point 414 (the bottom frame bridge portion includes a groove that engages the lens 416 of the lens carrier). The lens carrier 414 also includes side projections 418 that are configured to engage corresponding female attachment portions 420 on the safety eyewear frame 422 (see FIG. 7).

Figure 8:
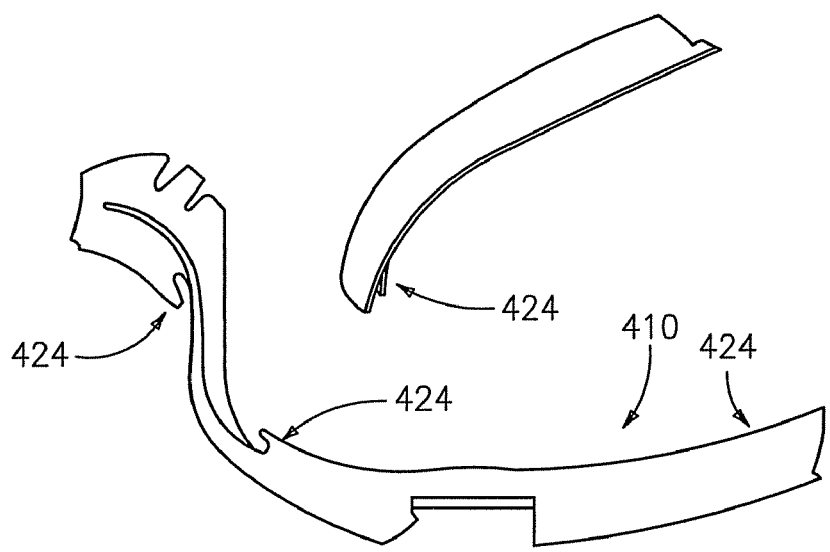
FIG. 8 is a perspective view of an exemplary removable lens carrier frame.

With reference to FIG. 8, the exemplary removable lens carrier 410 may itself permit interchange or removal of the lens 416. Lens grooves 424 may be seen around the lens carrier 410.

Figure 10:
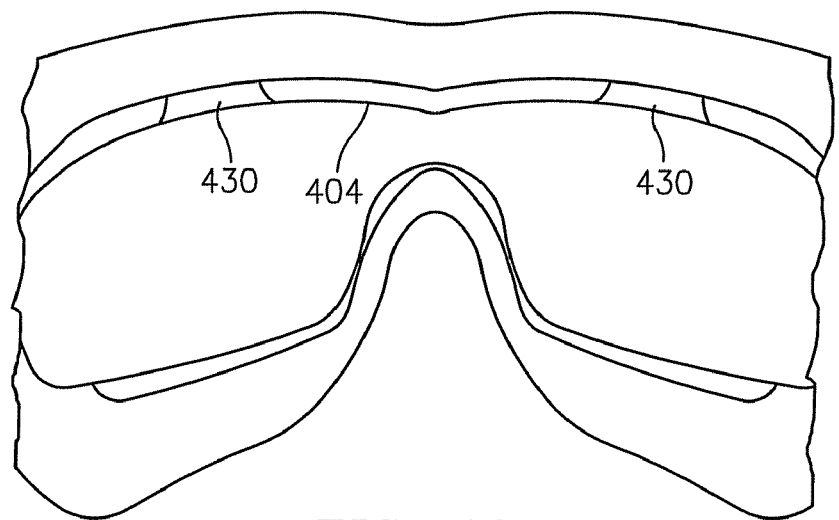
FIG. 10 is a rear elevation view of an exemplary safety eyewear.
Figure 9:
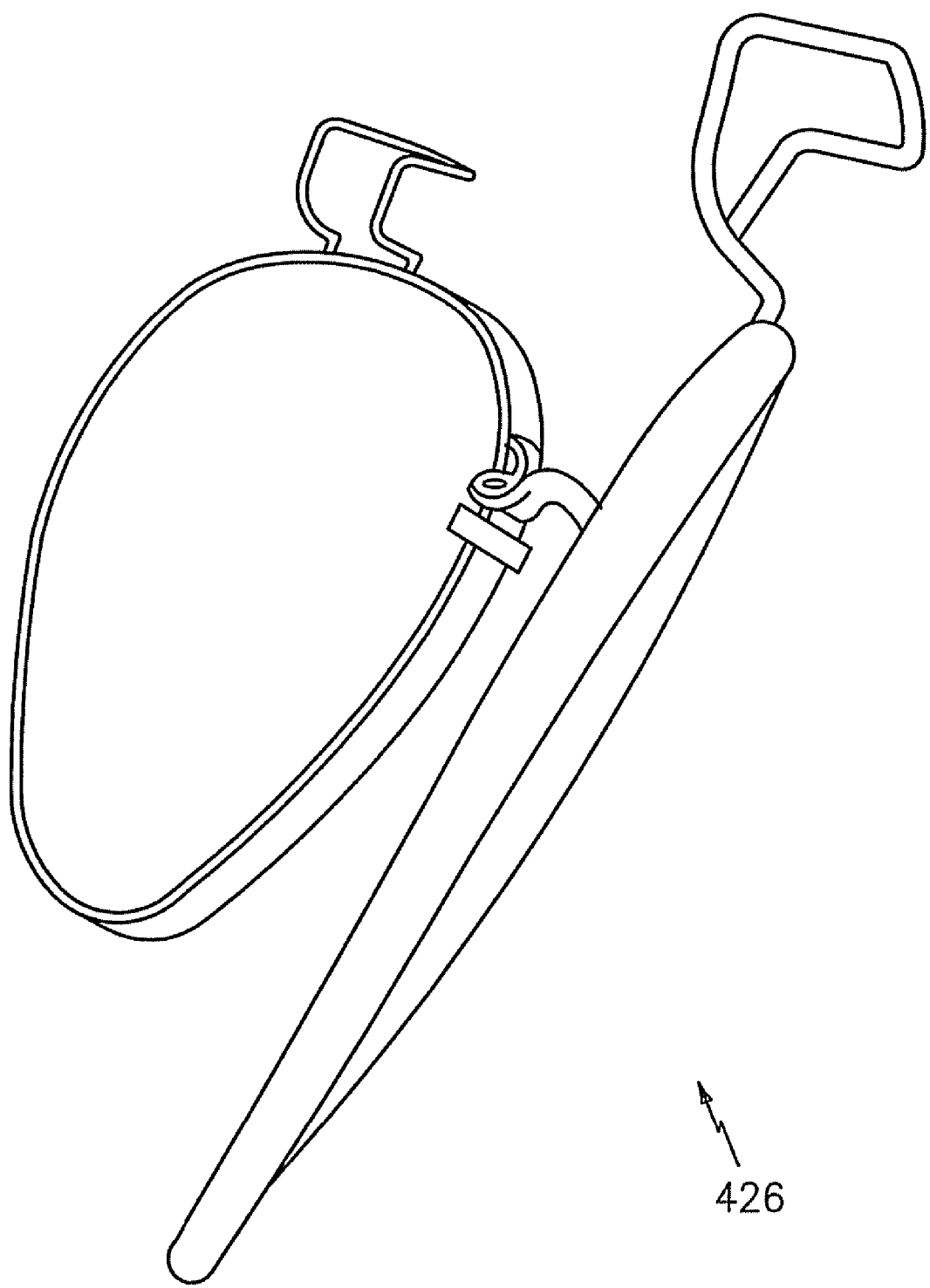
FIG. 9 is a side elevation view of an exemplary prescription insert.

Referring to FIG. 9, another exemplary prescription lens component is illustrated generally at 426. In relevant part, the exemplary prescription lens component 426 includes an attachment 428 that will permit interchange of the removable lens carrier 410 without necessitating detachment of the prescription lens component 426. In the illustrated exemplary embodiment, the attachment embodies wire hook portions that engage corresponding slots 430 in the safety eyewear frame 404 (see FIG. 10).

Figure 11:
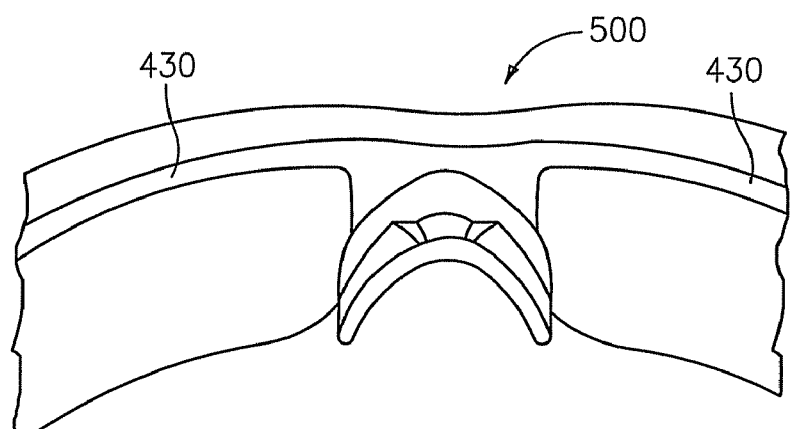
FIG. 11 is a top elevation view of an exemplary second safety eyewear including prescription insert attachment points.

In an exemplary embodiment, a second exemplary safety eyewear 500 (See FIG. 11) also includes corresponding slots 430, such that the prescription lens component 426 may be interchanged between plural different safety eyewear. Such cross platform compatibility may be arranged such that there is no requirement for adjustment or compensation of the prescription insert when the insert is switched between different eyewear, that is, the prescription insert may be positioned in the same way relative to the eyes. In another embodiment, the safety eyewear may be configured with aspheric lens portions that maintain the effect of the prescription lens (e.g., the lens may be flat in the front and turn at the sides).

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A safety eyewear comprising:
a lens attached to a removable lens carrier; and
the lens carrier configured to be removably attached to a frame while said frame is engaged with the face of a user, the removable lens carrier and the frame extend from a bottom of a side portion of the lens across an upper portion of the lens to a bottom of an opposite side portion of the lens wherein the safety eyewear provides a user with an unobstructed field of vision in a vertical direction during use.

2. Safety eyewear in accordance with claim 1, wherein the attached lens is permanently attached to the removable lens carrier.

3. Safety eyewear in accordance with claim 1, wherein the removable lens carrier engages the safety eyewear frame at side peripheral portions via projections on the removable lens carrier that engage corresponding female portions on the safety eyewear frame.

4. Safety eyewear in accordance with claim 3, wherein the removable lens carrier engages the safety eyewear frame at an upper portion between the orbital lens portions and at a lower bridge portion.

5. Safety eyewear in accordance with claim 1, wherein the unobstructed portion comprises at least an two centimeters of lens bottom on each orbital wherein the frame is not overlying the viewable lens portion.

6. Safety eyewear in accordance with claim 5, wherein the unobstructed portion comprises at least an three centimeters of lens bottom on each orbital wherein the frame is not overlying the viewable lens portion.

* * * * *

UNITED STATES PATENT AND TRADEMARK OFFICE
CERTIFICATE OF CORRECTION

| | |
|---|---|
| PATENT NO. | : 7,527,373 B2 |
| APPLICATION NO. | : 11/758868 |
| DATED | : May 5, 2009 |
| INVENTOR(S) | : Glen Stanley |

Page 1 of 1

It is certified that error appears in the above-identified patent and that said Letters Patent is hereby corrected as shown below:

<u>On the Title Page, Related U.S. Application Data</u>
Delete "60/811,325" and insert therefore --60/811,181--.

Signed and Sealed this

Third Day of November, 2009

David J. Kappos
*Director of the United States Patent and Trademark Office*